United States Patent
Kim et al.

(10) Patent No.: US 11,732,107 B2
(45) Date of Patent: Aug. 22, 2023

(54) PLASTICIZER COMPOSITION INCLUDING CYCLOHEXANE 1,4-DIESTER-BASED COMPOUND AND RESIN COMPOSITION INCLUDING THE SAME

(71) Applicant: LG CHEM, LTD., Seoul (KR)

(72) Inventors: Hyun Kyu Kim, Daejeon (KR); Mi Yeon Lee, Daejeon (KR); Seok Ho Jeong, Daejeon (KR); Yun Ki Cho, Daejeon (KR); Jeong Ju Moon, Daejeon (KR); Joo Ho Kim, Daejeon (KR)

(73) Assignee: LG CHEM, LTD., Seoul (KR)

( * ) Notice: Subject to any disclaimer, the term of this patent is extended or adjusted under 35 U.S.C. 154(b) by 185 days.

(21) Appl. No.: 16/319,993

(22) PCT Filed: Dec. 26, 2017

(86) PCT No.: PCT/KR2017/015493
§ 371 (c)(1),
(2) Date: Jan. 23, 2019

(87) PCT Pub. No.: WO2018/128314
PCT Pub. Date: Jul. 12, 2018

(65) Prior Publication Data
US 2019/0248982 A1    Aug. 15, 2019

(30) Foreign Application Priority Data

Jan. 4, 2017    (KR) .................. 10-2017-0001572

(51) Int. Cl.
| | |
|---|---|
| *C08K 5/12* | (2006.01) |
| *C08F 14/06* | (2006.01) |
| *C07C 69/75* | (2006.01) |
| *C08J 5/18* | (2006.01) |
| *C08L 101/00* | (2006.01) |
| *C08K 5/00* | (2006.01) |

(52) U.S. Cl.
CPC .............. *C08K 5/12* (2013.01); *C07C 69/75* (2013.01); *C08F 14/06* (2013.01); *C08J 5/18* (2013.01); *C08K 5/00* (2013.01); *C08L 101/00* (2013.01); *C08J 2327/06* (2013.01); *C08K 2201/014* (2013.01)

(58) Field of Classification Search
CPC ....................................... C08K 5/12
See application file for complete search history.

(56) References Cited

U.S. PATENT DOCUMENTS

| | | | |
|---|---|---|---|
| 7,208,545 B1 | 4/2007 | Brunner et al. | |
| 7,973,194 B1 | 7/2011 | Kinkade et al. | |
| 10,407,559 B2 | 9/2019 | Miyazaki et al. | |
| 2011/0232825 A1* | 9/2011 | Mack ................. | C09K 3/10 156/71 |
| 2011/0263770 A1 | 10/2011 | Yoon et al. | |
| 2012/0138206 A1* | 6/2012 | Wagner ............... | C08K 5/12 156/60 |
| 2013/0053492 A1 | 2/2013 | Yoon et al. | |
| 2015/0007750 A1* | 1/2015 | Lee .................... | C07C 69/82 106/287.24 |
| 2016/0237244 A1 | 8/2016 | Boeck et al. | |
| 2017/0015810 A1 | 1/2017 | Miyazaki et al. | |
| 2018/0163018 A1 | 6/2018 | Kim et al. | |
| 2018/0171103 A1 | 6/2018 | Kim et al. | |
| 2018/0298161 A1 | 10/2018 | Kim et al. | |
| 2019/0248984 A1 | 8/2019 | Kim et al. | |

FOREIGN PATENT DOCUMENTS

| | | |
|---|---|---|
| CN | 1356973 A | 7/2002 |
| CN | 102822136 A | 12/2012 |
| CN | 106164164 A | 11/2016 |
| EP | 2810932 A1 | 12/2014 |
| EP | 2810982 A1 | 12/2014 |
| EP | 3293226 A1 | 3/2018 |
| EP | 3342794 A1 | 7/2018 |
| EP | 3434721 A1 | 1/2019 |
| JP | 2012-166483 A | 9/2012 |
| JP | 2014-034169 A | 2/2014 |
| JP | 5833625 B | 12/2015 |
| JP | 2016-022708 A | 2/2016 |
| KR | 10-2002-0010929 A | 2/2002 |
| KR | 10-2009-0038514 A | 4/2009 |
| KR | 10-1005704 B1 | 1/2011 |
| KR | 10-2016-0101880 A | 8/2016 |

OTHER PUBLICATIONS

English machine translation of (KR-10-2009-0038514).*

* cited by examiner

*Primary Examiner* — Michael F Pepitone
(74) *Attorney, Agent, or Firm* — Morgan, Lewis & Bockius LLP

(57) ABSTRACT

The present invention relates to a plasticizer composition in which three types of cyclohexane 1,4-diester-based compounds prepared through trans-esterification and hydrogenation are mixed, wherein alkyl substituents of the dicarboxylate are a 2-ethylhexyl group and a butyl group or an isobutyl group, which has fewer carbon atoms than the 2-ethylhexyl group, so that the plasticizer composition may exhibit excellent properties in terms of stress resistance, migration resistance, plasticization efficiency, and the like while maintaining an excellent level of tensile strength and elongation rate, when used for a resin composition.

6 Claims, No Drawings

PLASTICIZER COMPOSITION INCLUDING CYCLOHEXANE 1,4-DIESTER-BASED COMPOUND AND RESIN COMPOSITION INCLUDING THE SAME

CROSS-REFERENCE TO RELATED APPLICATIONS

This application is a National Stage Application of International Application No. PCT/KR2017/015493 filed on Dec. 26, 2017, which claims priority to and the benefit of Korean Patent Application No. 10-2017-0001572, filed on Jan. 4, 2017, the disclosure of which is incorporated herein by reference in its entirety.

TECHNICAL FIELD

Technical Field

The present invention relates to a plasticizer composition including a cyclohexane 1,4-diester-based compound(s) and a resin composition including the same, and more particularly, to a plasticizer composition including hydrogenated compounds derived from a terephthalate-based compound(s) having one or more compositions and a resin composition including the same.

Background Art

Conventionally, a plasticizer forms an ester through a reaction between an alcohol and a polycarboxylic acid such as phthalic acid or adipic acid. Commercially important examples of the ester include adipates of C8, C9, and C10 alcohols such as di(2-ethylhexyl) adipate, diisononyl adipate, and diisodecyl adipate; and phthalates of C8, C9, and C10 alcohols such as di(2-ethylhexyl) phthalate, diisononyl phthalate, and diisodecyl phthalate.

Specifically, di(2-ethylhexyl) phthalate is used in the manufacture of plastisol, toys, films, shoes, paint, flooring materials, gloves, wallpaper sheets, artificial leather, sealant, tarpaulins, car floor-coating agents, furniture, foam mats, and soundproofing panels through dry blending, and may also be used in the production of exterior and insulating materials for PVC cables and other calendered plastic PVC products.

As ester compounds currently used as a plasticizer, di(2-ethylhexyl) phthalate (DEHP), diisononyl phthalate (DINP), di(2-propylheptyl) phthalate (DPHP), diisodecyl phthalate (DIDP), and the like have been mainly used. However, these compounds are environmental hormones which disrupt the endocrine system and are harmful to the human body, and also have a limitation in improving properties of a product, such as processability of a resin, absorption rate, volatile loss, migration loss, thermal stability, and the like, depending on the area of application.

Accordingly, there is a need to develop a method of preparing an environmentally friendly or non-phthalate-based compound capable of sufficiently improving an existing product in terms of various properties such as processability of a resin, absorption rate, hardness, tensile strength, elongation rate, volatile loss, migration loss, thermal stability, and the like.

DISCLOSURE

Technical Problem

It is an object of the present invention to provide a plasticizer composition including, as a novel compound(s), one or more cyclohexane 1,4-diester-based compounds hydrogenated from one or more terephthalate-based compositions. It is another object of the present invention to provide a resin product in which migration resistance, plasticization efficiency, stress resistance, and the like are improved in a way that mechanical properties such as tensile strength and elongation rate are not sacrificed, by using the plasticizer composition including a cyclohexane 1,4-diester-based compound(s).

Technical Solution

According to an embodiment of the present invention, there is provided a plasticizer composition which includes a cyclohexane 1,4-diester-based compound represented by Chemical Formula 1 below, a cyclohexane 1,4-diester-based compound represented by Chemical Formula 2 below, and a cyclohexane 1,4-diester-based compound represented by Chemical Formula 3 below.

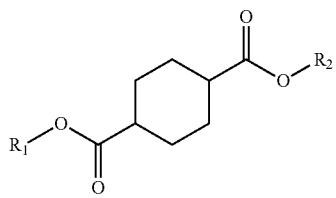

[Chemical Formula 1]

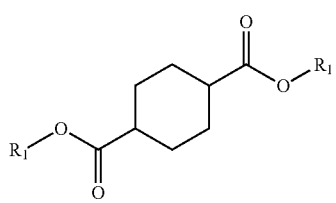

[Chemical Formula 2]

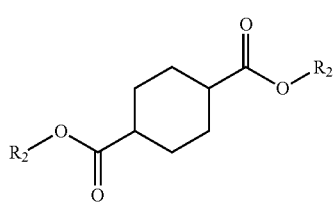

[Chemical Formula 3]

In Chemical Formulas 1 to 3, $R_1$ is a butyl group or an isobutyl group, and $R_2$ is a 2-ethylhexyl group.

The plasticizer composition may include the cyclohexane 1,4-diester-based compound represented by Chemical Formula 1, the cyclohexane 1,4-diester-based compound represented by Chemical Formula 2, and the cyclohexane 1,4-diester-based compound represented by Chemical Formula 3 at 0.5 to 70 wt %, 0.5 to 50 wt %, and 0.5 to 85 wt %, respectively, with respect to the total weight of the plasticizer composition.

In the plasticizer composition, the sum of the cyclohexane 1,4-diester-based compound represented by Chemical Formula 2 and the cyclohexane 1,4-diester-based compound represented by Chemical Formula 3 and the cyclohexane 1,4-diester-based compound represented by Chemical Formula 1 may be at a ratio of 95:5 to 30:70 by weight.

According to another embodiment of the present invention, there is provided a resin composition which includes 100 parts by weight of a resin; and 5 to 150 parts by weight of the above-described plasticizer composition.

The resin may include one or more selected from the group consisting of ethylene vinyl acetate, polyethylene, polypropylene, polyketone, polyvinyl chloride, polystyrene, polyurethane, a thermoplastic elastomer, and polylactic acid.

Advantageous Effects

A plasticizer composition prepared through trans-esterification and hydrogenation according to an embodiment of the present invention can impart excellent properties in terms of tensile strength, elongation rate, migration resistance, volatile resistance, and the like and provide a resin product having excellent stress resistance, when used for a resin composition.

Mode for Invention

Hereinafter, the present invention will be described in further detail to help in understanding the present invention.

Terms and words used in this specification and claims should not be interpreted as limited to commonly used meanings or meanings in dictionaries and should be interpreted with meanings and concepts which are consistent with the technological scope of the invention based on the principle that the inventors have appropriately defined concepts of terms in order to describe the invention in the best way.

Plasticizer Composition

According to an embodiment of the present invention, there is provided a plasticizer composition including a cyclohexane 1,4-diester-based compound represented by Chemical Formula 1 below.

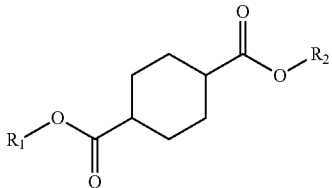

[Chemical Formula 1]

In Chemical Formula 1, $R_1$ is a butyl group or an isobutyl group, and $R_2$ is a 2-ethylhexyl group.

As described above, when a plasticizer composition includes a cyclohexane 1,4-diester-based compound in which a butyl group or an isobutyl group is bonded to an ester group present at one side, and a 2-ethylhexyl group is bonded to an ester group present at the other side, a resin product to which the plasticizer composition is applied may have improved migration ability and increased plasticization efficiency.

The reason why the improvement in properties is possible as described above is that an alkyl group bonded to the ester group present at an opposite side of the 2-ethylhexyl group has fewer carbon atoms than the 2-ethylhexyl group, and is preferably that the alkyl group bonded to the ester group present at an opposite side of the 2-ethylhexyl group is a butyl group or an isobutyl group having 4 carbon atoms. Therefore, it may be preferable that a cyclohexane 1,4-diester-based compound in which a 2-ethylhexyl group is bonded to one side and a butyl group or an isobutyl group is bonded to the other side, such as the compound represented by Chemical Formula 1, is included in a plasticizer composition.

Meanwhile, when an alkyl group having more carbon atoms than a 2-ethylhexyl group or an aromatic hydrocarbon such as a hydrocarbon having a benzene ring, not an aliphatic hydrocarbon is bonded to the ester group present at an opposite side of a 2-ethylhexyl group, poor properties in terms of migration upon compression, migration upon stress, plasticization efficiency, and the like may result, and thus this case may not be preferable.

In addition, the plasticizer composition may further include a cyclohexane 1,4-diester-based compound represented by Chemical Formula 2 below and a cyclohexane 1,4-diester-based compound represented by Chemical Formula 3 below.

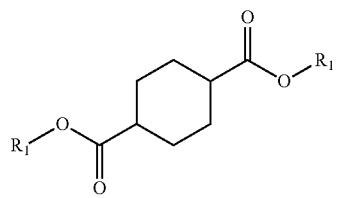

[Chemical Formula 2]

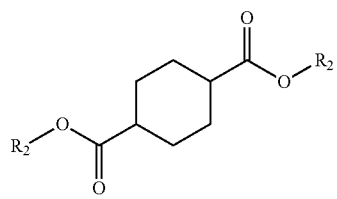

[Chemical Formula 3]

In Chemical Formulas 2 and 3, $R_1$ is a butyl group or an isobutyl group, and $R_2$ is a 2-ethylhexyl group.

As described above, when the plasticizer composition includes the cyclohexane 1,4-diester-based compounds represented by Chemical Formulas 2 and 3 in addition to the cyclohexane 1,4-diester-based compound represented by Chemical Formula 1, stress resistance may be improved, and plasticization efficiency may also be improved.

The plasticizer composition may be a composition including one or more cyclohexane 1,4-diester-based compounds in which carboxylate groups are bonded to carbons at 1- and 4-positions of cyclohexane. As described above, the use of cyclohexane 1,4-diester-based compound represented by Chemical Formula 1 for a plasticizer composition results in improved properties. However, when the compound represented by Chemical Formula 1 is used in combination with the compounds represented by Chemical Formulas 2 and 3, other properties may also be improved, and therefore, a plasticizer composition having generally excellent properties may be achieved.

Specifically, when the plasticizer composition includes one or more compounds, for example, three types of cyclohexane 1,4-diester-based compounds, the plasticizer composition may include butyl(2-ethylhexyl) cyclohexane-1,4-dicarboxylate (1,4-BEHCH) as the compound represented by Chemical Formula 1, dibutyl cyclohexane-1,4-dicarboxylate (1,4-DBCH) as the compound represented by Chemical Formula 2, and bis(2-ethylhexyl) cyclohexane-1,4-dicarboxylate (1,4-DEHCH) as the compound represented by Chemical Formula 3.

Alternatively, the plasticizer composition may include isobutyl(2-ethylhexyl) cyclohexane-1,4-dicarboxylate (1,4-iBEHCH) as the compound represented by Chemical Formula 1, diisobutyl cyclohexane-1,4-dicarboxylate (1,4-

DiBCH) as the compound represented by Chemical Formula 2, and bis(2-ethylhexyl) cyclohexane-1,4-dicarboxylate (1,4-DEHCH) as the compound represented by Chemical Formula 3.

The plasticizer composition may include the cyclohexane 1,4-diester-based compound represented by Chemical Formula 1, the cyclohexane 1,4-diester-based compound represented by Chemical Formula 2, and the cyclohexane 1,4-diester-based compound represented by Chemical Formula 3 at 0.5 to 70 wt %, 0.5 to 50 wt %, and 0.5 to 85 wt %, respectively, with respect to the total weight of the plasticizer composition.

Preferably, the plasticizer composition includes the cyclohexane 1,4-diester-based compound represented by Chemical Formula 1, the cyclohexane 1,4-diester-based compound represented by Chemical Formula 2, and the cyclohexane 1,4-diester-based compound represented by Chemical Formula 3 at 10 to 50 wt %, 0.5 to 50 wt %, and 35 to 80 wt %, respectively, with respect to the total weight of the plasticizer composition.

The plasticizer composition according to the present invention includes cyclohexane 1,4-diester-based compounds respectively represented by Chemical Formulas 1 to 3, as described above. In this case, a weight average carbon number as determined based on a carbon number and a weight ratio may be about 5.7 to 7.9, preferably 6.2 to 7.7, and more preferably 6.4 to 7.5. When the weight average carbon number is within the above range, an appropriately adjusted absorption rate may be attained, excellent processability due to a short melt time may result, and plasticization efficiency and migration resistance may be improved while mechanical properties such as tensile strength and elongation rate are maintained at sufficient levels.

The term "weight average carbon number" used herein refers to a value obtained by averaging the average carbon number of two alkyl groups bonded to a diester group of each terephthalate component by using the weight fraction of each terephthalate component. For example, the weight average carbon number may be defined by Equation 1 below.

$$N_c = \sum_{i=1}^{n} C_i w_i \qquad \text{[Equation 1]}$$

In Equation 1, $N_c$ is a weight average carbon number, $C_i$ is the average carbon number of two alkyl groups bonded to a diester group of each terephthalate component, and $w_i$ is the weight fraction of each terephthalate component.

Specifically, when a terephthalate-based compound includes first to $n^{th}$ components, the weight average carbon number may be the sum of a value obtained by multiplying an average carbon number ($C_1$) of two alkyl groups of a first component by the weight fraction ($w_1$) of the first component, a value obtained by multiplying an average carbon number ($C_2$) of two alkyl groups of a second component by the weight fraction ($w_2$) of the second component, and a value obtained by multiplying an average carbon number ($C_n$) of two alkyl groups of a $n^{th}$ component by the weight fraction ($w_n$) of the $n^{th}$ component.

For example, when three components, namely the compound represented by Chemical Formula 2, the compound represented by Chemical Formula 1, and the compound represented by Chemical Formula 3, are included at 5 wt %, 40 wt %, and 55 wt %, respectively, the weight average carbon number is (0.05×4)+(0.4×6)+(0.55×8)=7.

In the plasticizer composition, the sum of the cyclohexane 1,4-diester-based compound represented by Chemical Formula 2 and the cyclohexane 1,4-diester-based compound represented by Chemical Formula 3 and the cyclohexane 1,4-diester-based compound represented by Chemical Formula 1 may be at a ratio of 95:5 to 30:70 by weight.

That is, the compound represented by Chemical Formula 2 and the compound represented by Chemical Formula 3 may be compounds derived from a dual attack ester compound and a reaction residual ester compound in trans-esterification and may be non-hybrid types because the same alkyl groups are bonded to a dicarboxylate group of cyclohexane. The compound represented by Chemical Formula 1 may be a compound derived from a single attack ester compound and may be a hybrid type. That is, it may be understood that the non-hybrid-type compounds and the hybrid-type compound are included at a weight ratio of 95:5 to 30:70.

Detailed descriptions of the dual attack ester compound, single attack ester compound, and residual ester compound will be described below.

When used as a plasticizer for a resin composition, the plasticizer composition may ensure the same levels of hardness, tensile strength, and elongation rate as those provided by a conventionally mainly used plasticizer such as a phthalate-based compound, and may result in reduced volatile loss, significantly high migration resistance, and excellent stress resistance.

Method of Preparing Plasticizer Composition

According to an embodiment of the present invention, there is provided a method of preparing a plasticizer composition, which includes preparing an ester-based composition by performing trans-esterification of a diester-based compound with an alcohol; and preparing a cyclohexane 1,4-diester-based compound composition by performing hydrogenation of the ester-based composition in the presence of a metal catalyst, wherein the diester-based compound includes di(2-ethylhexyl) terephthalate (DEHTP).

The method of preparing a plasticizer composition may include preparing an ester-based composition in which three types of ester-based compounds are mixed, by performing trans-esterification of a diester-based compound with an alcohol.

The diester-based compound used as a reactant in trans-esterification may be di(2-ethylhexyl) terephthalate, wherein a 2-ethylhexyl group, which is a substituent in which an ethyl group is bonded to a carbon at 2-position of a hexyl group having 6 carbon atoms, forming a branch, may have a total of 8 carbon atoms, and may be interchangeably used with an "octyl group" in the specification.

In addition, the alcohol may be any one selected from the group consisting of isobutyl alcohol and n-butyl alcohol.

The term "trans-esterification" used herein refers to a reaction between an alcohol and an ester as shown in Reaction Scheme 1, in which R" of the ester is interchanged with R' of the alcohol:

[Reaction Scheme 1]

The trans-esterification may produce: a compound (hereinafter, referred to as a "dual attack ester compound")

formed by an alkoxide of the alcohol attacking two carbons of carbonyl groups of two ester (RCOOR") groups present in the dioctyl terephthalate; a compound (hereinafter, referred to as a "single attack ester compound") formed by an alkoxide of the alcohol attacking one carbon of one ester (RCOOR") group; and a compound (hereinafter, referred to as a "reaction residual ester compound") remaining as an non-reactant, which did not participate in the reaction.

The trans-esterification may be performed without a catalyst. Accordingly, the trans-esterification does not cause water contamination, unlike acid-alcohol esterification, and may solve problems caused by the use of an acidic catalyst.

The above-described trans-esterification may produce three types of compounds: the single attack ester compound, the dual attack ester compound, and the reaction residual ester compound at 0.5 wt % to 70 wt %, 0.5 wt % to 50 wt %, and 0.5 wt % to 85 wt %, specifically 10 wt % to 50 wt %, 0.5 wt % to 50 wt %, and 35 wt % to 80 wt %, respectively, with respect to the total weight of the ester-based composition.

When an ester-based composition including the ester compounds within the above content ranges is used to prepare a plasticizer composition, a plasticizer composition having high processing efficiency, excellent processability, and excellent absorption rate may be achieved.

The ester-based composition prepared through the trans-esterification may include all three types of ester compounds, namely the single attack ester compound, the dual attack ester compound, and the reaction residual ester compound, and a composition ratio of the ester-based composition may be controlled according to an addition amount of the alcohol.

The addition amount of the alcohol may be 0.1 to 89.9 parts by weight, specifically 3 to 50 parts by weight, and more specifically 5 to 40 parts by weight with respect to 100 parts by weight of the diester-based compound, that is, the dioctyl terephthalate.

As more alcohol is used, a higher mole fraction of the diester-based compound may be involved in the trans-esterification in the preparation of the ester-based composition. Accordingly, contents of the single attack ester compound and the dual attack ester compound may increase in the plasticizer composition.

On the other hand, a content of the reaction residual ester compound remaining unreacted may tend to decrease.

A molar ratio of the diester-based compound and the alcohol may be, for example, 1:0.005 to 5.0, 1:0.05 to 2.5, or 1:0.1 to 1.0. Within this range, it is possible to obtain an ester-based composition capable of providing a plasticizer composition having high processing efficiency and a high effect of improving processability.

The trans-esterification may be performed at a temperature of 120 to 190° C., preferably 135 to 180° C., and more preferably 141 to 179° C. for 10 minutes to 10 hours, preferably 30 minutes to 8 hours, and more preferably 1 to 6 hours. Within the above temperature and time ranges, an ester-based composition having a desired composition ratio may be effectively obtained. In this case, the reaction time may be calculated from the point of time at which the reaction temperature is reached after raising the temperature of the reactants.

The trans-esterification may be performed without a catalyst, but in some cases, it may be performed in the presence of an acidic catalyst or a metal catalyst, which provides an effect of reducing a reaction time.

Examples of the acidic catalyst include sulfuric acid, methanesulfonic acid, p-toluenesulfonic acid, and the like, and examples of the metal catalyst include an organometallic catalyst, a metal oxide catalyst, a metal salt catalyst, and a metal itself.

A metal component of the metal catalyst may be, for example, any one or a mixture of two or more selected from the group consisting of tin, titanium, and zirconium.

The method of preparing a plasticizer composition may further include removing an unreacted alcohol and a reaction by-product, for example, a diester-based compound, through distillation after the trans-esterification.

The distillation may be, for example, two-step distillation in which the alcohol and the reaction by-product are separated due to different boiling points thereof or mixed distillation. In this case, it is possible to relatively accurately ensure a desired composition ratio of the ester-based composition. The mixed distillation refers to a process of distilling butanol and a reaction by-product at the same time.

As described above, the diester-based compound in the trans-esterification may be di(2-ethylhexyl) terephthalate, and the alcohol may be butyl alcohol and/or isobutyl alcohol.

The types of ester compounds included in the produced ester-based composition may vary depending on a combination of the diester-based compound and the alcohol used in the trans-esterification. Accordingly, a specific combination of compounds in a finally prepared plasticizer composition including a cyclohexane 1,4-diester-based compound may vary.

The method of preparing a plasticizer composition may include converting ester compounds constituting the ester-based composition into a composition which is a mixture of cyclohexane 1,4-diester-based compounds by performing hydrogenation of the ester-based composition in the presence of a metal catalyst.

The hydrogenation is a reaction for eliminating the aromaticity of a benzene ring of the ester-based composition by adding hydrogen in the presence of a metal catalyst, and may be a type of a reduction reaction.

The hydrogenation is a reaction for synthesizing a composition which is a mixture of cyclohexane 1,4-diester-based compounds by reacting the ester-based composition with hydrogen in the presence of a metal catalyst, and conditions for this reaction may include all of the conventional reaction conditions for hydrogenating only benzene rings while not affecting carbonyl groups substituted in the benzene.

The hydrogenation may be performed with an additional organic solvent such as ethanol or the like, but the present invention is not limited thereto. The metal catalyst may be an Rh/C catalyst, a Pt catalyst, a Pd catalyst, or the like, which is generally used to hydrogenate a benzene ring, and any one capable of being used in the hydrogenation is used without limitation.

When a cyclohexane 1,4-diester-based compound or a mixed composition thereof is prepared from a terephthalate-based compound through hydrogenation, component ratios of the terephthalate-based compound may be maintained almost at the equivalent level, whether the terephthalate-based compound is a single compound or a mixture of a plurality of compounds.

The method of preparing a plasticizer composition according to the present invention may further include preparing a diester-based compound used in the trans-esterification through direct esterification of a dicarboxylic acid-based compound with an alcohol in the presence of a catalyst.

In the direct esterification, the dicarboxylic acid-based compound may include terephthalic acid, and the alcohol may include 2-ethylhexyl alcohol.

The direct esterification may be performed at 80 to 270° C., preferably 150 to 250° C. for 10 minutes to 10 hours, preferably 30 minutes to 8 hours, and more preferably 1 to 6 hours. Within the above temperature and time ranges, the diester-based compound may be effectively obtained.

The catalyst used in the direct esterification may be an organometallic catalyst such as a Sn-based or Ti-based catalyst, an acidic catalyst such as a sulfonic acid-based or sulfuric acid-based catalyst, or a combination thereof, but a type of catalyst is not limited thereto.

The dicarboxylic acid-based compound and the alcohol are used at a molar ratio of 1:1 to 7, preferably 1:2 to 5.

The alcohol may be prepared by a common method or may be a commercially available product. When a commercially available product is used, the alcohol may be included in combination with one or more isomers thereof. In this case, the alcohol and the isomers thereof being used may be, for example, at a ratio of 50 to 100 parts by weight:0 to 50 parts by weight, preferably 70 to 100 parts by weight:0 to 30 parts by weight.

According to an embodiment of the present invention, when the alcohol is used in combination with the isomers thereof, a mixture of a diester-based compound and an isomer thereof may be prepared. Accordingly, the ester-based composition according to an embodiment of the present invention may further include a plurality of isomers of each ester compound.

Through the direct esterification for preparing the diester-based compound according to an embodiment of the present invention, the diester-based compound may be prepared with a yield of about 80% or more, and trans-esterification of the diester-based compound thus prepared with the alcohol may be performed to easily prepare an ester-based composition consisting of desired components mixed at a desired composition ratio.

As another example, the order of esterification and hydrogenation in the method of preparing a plasticizer composition may be changed; however, in this case, the same composition may be prepared. That is, a cyclohexane 1,4-diester-based compound substance including a hybrid-type compound and a non-hybrid-type compound may be prepared by performing hydrogenation of the diester-based compound to eliminate a double bond of a benzene ring to prepare a cyclohexane 1,4-diester-based compound and then performing trans-esterification of the cyclohexane 1,4-diester-based compound with an alcohol.

Alternatively, the cyclohexane 1,4-diester-based substance may be prepared by using 1,4-cyclohexanedicarboxylic acid instead of terephthalic acid as a raw material. In this case, a cyclohexane 1,4-diester-based substance which is a single compound may be prepared through direct esterification of 1,4-cyclohexanedicarboxylic acid with one alcohol, and a cyclohexane 1,4-diester-based substance which is a mixture of a plurality of compounds may be prepared through direct esterification of 1,4-cyclohexanedicarboxylic acid with two or more alcohols or through direct esterification of 1,4-cyclohexanedicarboxylic acid with one alcohol and subsequent trans-esterification with another alcohol.

In addition, dimethyl cyclohexane 1,4-diester may be used instead of 1,4-cyclohexanedicarboxylic acid. In this case, a cyclohexane 1,4-diester-based substance which is a single compound or a mixture of a plurality of compounds may be prepared through esterification just as when the dicarboxylic acid is used.

As described above, the cyclohexane 1,4-diester-based substance may be prepared without performing hydrogenation, and this method may reduce a risk involved in the process or a burden of high processing costs caused by hydrogenation. However, a method of preparing a cyclohexane 1,4-diester-based substance is not particularly limited as long as it prepares a cyclohexane 1,4-diester-based substance including a compound represented by Chemical Formula 1.

According to another embodiment of the present invention, there is provided a resin composition including the above-described plasticizer composition and a resin.

The resin may be a resin known in the related art. For example, the resin is a mixture of one or more selected from ethylene vinyl acetate, polyethylene, polypropylene, polyvinyl chloride, polyketone, polystyrene, polyurethane, a thermoplastic elastomer, and polylactic acid, but the present invention is not limited thereto.

The plasticizer composition may be included in an amount of 5 to 150 parts by weight, preferably 5 to 80 parts by weight, and more preferably 10 to 60 parts by weight with respect to 100 parts by weight of the resin.

In addition, the resin composition may further include various additives as necessary, and the additives may be appropriately selected according to a purpose of use. Also, the resin composition may be applied in the preparation of one or more selected from the group consisting of electric wires, flooring materials, interior materials for automobiles, films, sheets, wallpaper sheets, and tubes.

EXAMPLES

Hereinafter, the present invention will be described in detail with reference to embodiments. However, the embodiments of the present invention may be modified in several different forms, and the scope of the present invention is not limited to the embodiments to be described below. The embodiments of the present invention are provided so that this disclosure will be thorough and complete, and will fully convey the concept of embodiments to those skilled in the art.

Example 1

1) Esterification 2,000 g of di(2-ethylhexyl) terephthalate (DEHTP) and 340 g (17 parts by weight with respect to 100 parts by weight of DEHTP) of n-butanol were added to a reaction vessel equipped with a stirrer, a condenser, and a decanter, and then trans-esterification was performed at a reaction temperature of 160° C. under a nitrogen atmosphere for 2 hours, thereby obtaining an ester-based plasticizer composition including dibutyl terephthalate (DBTP), butyl(2-ethylhexyl) terephthalate (BEHTP), and di(2-ethylhexyl) terephthalate (DEHTP) at 4 wt %, 35 wt %, and 61 wt %, respectively.

The ester-based plasticizer composition was subjected to mixed distillation to remove butanol and 2-ethylhexyl alcohol, thereby finally preparing a mixed composition.

2) Hydrogenation 1,000 g of the composition produced through the esterification and 20 g of a ruthenium catalyst (N.E CHEMCAT) were added as raw materials to a 1.5 L high-pressure reaction vessel, and hydrogen was added under a pressure of 8 MPa to perform hydrogenation at 150° C. for 3 hours, and then the reaction was completed. After the reaction was completed, the catalyst was filtered, and a conventional purification process was performed, thereby preparing a hydrogenated mixed composition with a yield of 99%.

Example 2

1) Esterification 498.0 g of purified terephthalic acid (PTA), 585 g of 2-ethylhexyl alcohol (2-EH) (a molar ratio of PTA:2-EH=1.0:1.5), and 333 g of butyl alcohol (BA) (a molar ratio of PTA:BA=1.0:1.5) were added to a 3 L four-neck reaction vessel equipped with a cooler, a condenser, a decanter, a reflux pump, a temperature controller, a stirrer, and the like. 10 g (2.0 parts by weight with respect to 100 parts by weight of PTA) of a sulfonic acid-based catalyst (methane sulfonic acid (MSA)) was added thereto, and then the temperature of the reaction vessel was slowly raised up to about 150° C. The generation of produced water started at about 130° C., and esterification was performed at a final reaction temperature of about 220° C. under an atmospheric pressure condition for about 4.5 hours while continuously introducing nitrogen gas and was terminated when an acid value reached 6.0.

After the reaction was completed, distillation extraction was performed under reduced pressure for 0.5 to 4 hours to remove unreacted raw materials. To reduce the level of the unreacted raw materials to a predetermined content level or less by removing the same, steam extraction was performed under reduced pressure using steam for 0.5 to 3 hours. A temperature of a reaction solution was cooled to about 90° C., and neutralization treatment was performed using an alkaline solution. In this case, washing may be optionally performed. Thereafter, the reaction solution was dehydrated to remove water. A filtering material was introduced into the dehydrated reaction solution, stirred for a predetermined period of time, and then filtered, thereby finally obtaining a mixed composition.

2) Hydrogenation

A hydrogenated mixed composition was prepared by performing hydrogenation of the mixed composition in the same manner as in Example 1.

Example 3

516.0 g of 1,4-cyclohexanedicarboxylic acid (CHDA), 897 g of 2-ethylhexyl alcohol (2-EH) (a molar ratio of CHDA:2-EH=1.0:2.3), and 155 g of butyl alcohol (BA) (a molar ratio of CHDA:BA=1.0:0.7) were added to a 3 L four-neck reaction vessel equipped with a cooler, a condenser, a decanter, a reflux pump, a temperature controller, a stirrer, and the like. 10 g (2.0 parts by weight with respect to 100 parts by weight of CHDA) of a sulfonic acid-based catalyst (MSA) was added thereto, and then the temperature of the reaction vessel was slowly raised up to about 150° C. The generation of produced water started at about 130° C., and esterification was performed at a final reaction temperature of about 220° C. under an atmospheric pressure condition for about 4.5 hours while continuously introducing nitrogen gas and was terminated when an acid value reached 6.0.

After the reaction was completed, distillation extraction was performed under reduced pressure for 0.5 to 4 hours to remove unreacted raw materials. To reduce the level of the unreacted raw materials to a predetermined content level or less by removing the same, steam extraction was performed under reduced pressure using steam for 0.5 to 3 hours. A temperature of a reaction solution was cooled to about 90° C., and neutralization treatment was performed using an alkaline solution. In this case, washing may be optionally performed. Thereafter, the reaction solution was dehydrated to remove water. A filtering material was introduced into the dehydrated reaction solution, stirred for a predetermined period of time, and then filtered, thereby finally obtaining a mixed composition.

Comparative Example 1

A mixed composition of dibutyl cyclohexane 1,4-diester, butylbenzyl cyclohexane 1,4-diester, and dibenzyl cyclohexane 1,4-diester was prepared in the same manner as in Example 1 except that benzyl alcohol was used instead of n-butanol.

Comparative Example 2

A mixed composition of diisononyl cyclohexane 1,4-diester, isononyl(2-ethylhexyl) cyclohexane 1,4-diester, and di(2-ethylhexyl) cyclohexane 1,4-diester was prepared in the same manner as in Example 1 except that isononanol was used instead of butanol.

Comparative Example 3

A composition was prepared by using di(2-ethylhexyl) cyclehexane 1,4-diester (LG Chem) alone.

Comparative Example 4

A composition was prepared by using dibutyl cyclohexane 1,4-diester (LG Chem) alone.

Comparative Example 5

A mixed composition of dibutyl cyclohexane 1,2-diester, butyl(2-ethylhexyl) cyclohexane 1,2-diester, and di(2-ethylhexyl) cyclohexane 1,2-diester was prepared in the same manner as in Example 1 except that phthalic anhydride was used instead of terephthalic acid.

Composition ratios of the compositions according to Examples 1 to 3 and Comparative Examples 1 to 5 are shown in Table 1 below.

TABLE 1

| | Compound represented by Chemical Formula 2 | Compound represented by Chemical Formula 1 | Compound represented by Chemical Formula 3 |
|---|---|---|---|
| Example 1 | 4 (1,4-DBCH) | 35 (1,4-BEHCH) | 61 (1,4-DEHCH) |
| Example 2 | 16 (1,4-DBCH) | 48 (1,4-BEHCH) | 36 (1,4-DEHCH) |
| Example 3 | 2 (1,4-DBCH) | 25 (1,4-BEHCH) | 73 (1,4-DEHCH) |
| Comparative Example 1 | 3 (1,4-DBCH) | 31 (1,4-BBeCH) | 66 (1,4-DBeCH) |
| Comparative Example 2 | 6 (1,4-DINCH) | 38 (1,4-INEHCH) | 56 (1,4-DEHCH) |
| Comparative Example 3 | — | — | 100 (1,4-DEHCH) |
| Comparative Example 4 | 100 (1,4-DBCH) | — | — |
| Comparative Example 5 | 3 (1,2-DBCH) | 34 (1,2-BEHCH) | 63 (1,2-DEHCH) |

Experimental Example 1

Specimen Preparation and Performance Evaluation

The plasticizers according to Examples 1 to 3 and Comparative Examples 1 to 5 were used as experimental specimens. For specimen preparation, referring to ASTM D638, 40 parts by weight of each of the plasticizers and 3 parts by weight of a stabilizer (LOX 912 NP) were mixed with 100 parts by weight of PVC in a mixer, and the resulting mixture was then subjected to roll-milling at 170° C. for 4 minutes and pressed for 2.5 minutes (low pressure) and 2 minutes (high pressure) at 180° C. using a press, thereby manufacturing 1 T and 3 T sheets. Each specimen was subjected to tests for the following properties, the results of which are shown in Table 2 below.

<Test Items>

Measurement of Hardness

According to ASTM D2240, Shore hardness (Shore "A") was measured at 25° C.

Measurement of Tensile Strength

According to ASTM D638, each specimen was pulled at a cross head speed of 200 mm/min using a universal testing machine (UTM) (Manufacturer; Instron, Model No.; 4466), and a point at which the specimen was broken was then determined. The tensile strength was calculated as follows:

Tensile strength(kgf/cm$^2$)=Load value(kgf)/Thickness (cm)×Width(cm)

Measurement of Elongation Rate

According to ASTM D638, each specimen was pulled at a cross head speed of 200 mm/min using a universal testing machine (UTM), and a point at which the specimen was broken was then determined. The elongation rate was calculated as follows:

Elongation rate (%)=Length after elongation/Initial length×100

Measurement of Migration Loss

A specimen having a thickness of 2 mm or more was obtained according to KSM-3156, ABS (natural color) was attached to both sides of the specimen, and a load of 1 kgf/cm$^2$ was then applied thereto. The specimen was placed in a hot-air convection oven (80° C.) for 72 hours, then taken out of the oven, and cooled at room temperature for 4 hours. Thereafter, the ABS attached to both sides of the specimen were removed, weights of the specimen before and after being placed in the oven were measured, and thus a migration loss was calculated by the equation as follows.

Migration loss(%)={(Initial weight of specimen at room temperature–Weight of specimen after being placed in oven)/Initial weight of specimen at room temperature}×100

Measurement of Volatile Loss

The prepared specimen was processed at 100° C. for 72 hours, and then a weight of the specimen was measured.

Volatile loss(%)=Initial weight of specimen–(Weight of specimen after being processed at 100° C. for 72 hours)/Initial weight of specimen×100

Stress Test

A stress test was performed by maintaining a specimen in a bent state at room temperature for 24 hours, 72 hours, and 168 hours, and a degree of migration (degree of leakage) was then observed and expressed as a numerical value. In the test, values closer to 0 indicate excellent characteristics.

TABLE 2

|  | Hardness (Shore "A") | Tensile strength (kgf/cm$^2$) | Elongation rate (%) | Migration loss (%) | Volatile loss (%) | Stress test |
|---|---|---|---|---|---|---|
| Example 1 | 82.4 | 248.0 | 276.1 | 1.24 | 1.74 | 0.5 |
| Example 2 | 81.9 | 243.3 | 277.1 | 0.50 | 2.84 | 0 |
| Example 3 | 82.9 | 251.2 | 280.6 | 1.35 | 1.45 | 0.5 |
| Comparative Example 1 | 85.2 | 245.0 | 270.5 | 1.77 | 1.54 | 1.5 |
| Comparative Example 2 | 86.0 | 229.4 | 275.2 | 1.53 | 0.90 | 2.0 |
| Comparative Example 3 | 85.7 | 228.6 | 273.3 | 1.73 | 1.70 | 2.0 |
| Comparative Example 4 | 75.6 | 188.6 | 256.3 | 5.60 | 12.50 | 1.0 |
| Comparative Example 5 | 80.8 | 223.0 | 254.9 | 1.15 | 2.28 | 0.5 |

Referring to Table 2, it can be confirmed that all of Examples 1 to 3 exhibited excellent properties compared to Comparative Examples 1 to 5 and had uniformly excellent properties.

Specifically, it can be confirmed that Comparative Example 2 to which an alkyl group having a large carbon number was applied and Comparative Example 1 to which an aromatic ring was applied exhibited high hardness, and thus lower plasticization efficiency than those of Examples 1 to 3. Also, it can be confirmed that Comparative Examples 1 and 2 exhibited a significantly high degree of migration upon stress and relatively poor mechanical properties in terms of elongation rate and tensile strength.

In addition, it can be confirmed that a few properties of Comparative Examples 3 and 4 to which a single compound was applied were particularly poor. In particular, Comparative Example 3 exhibited poor plasticization efficiency (high hardness) and a high degree of migration upon stress, and Comparative Example 4 exhibited significantly poor mechanical properties in terms of tensile strength and elongation rate and exhibited high migration loss and high volatile loss. However, it can be confirmed that Examples 1 to 3, in which weaknesses of Comparative Examples 3 and 4 have been complemented, exhibited an improvement in all of the above-mentioned properties, especially in tensile strength, elongation rate, and migration upon stress, compared to those of Comparative Examples 3 and 4.

Additionally, it can be confirmed that Comparative Example 5, in which a hydrogenated substance derived from a terephthalate-based compound was used, exhibited relatively poor properties compared to Examples 1 to 3, not to mention the inability to avoid causing environmental problems in the preparation process.

Accordingly, it was confirmed that, when a hydrogenated substance to which each of C4 and C8 alkyl groups was applied is used as a plasticizer, particularly, in consideration of a weight average carbon number thereof as in the case of Examples 1 to 3 according to the present invention, migration ability and plasticization efficiency can be improved while excellent mechanical properties in terms of tensile strength and elongation rate are being maintained, and, particularly, migration upon stress can be significantly improved.

The invention claimed is:

1. A plasticizer composition comprising:

a cyclohexane 1,4-diester-based compound represented by Chemical Formula 1;

a cyclohexane 1,4-diester-based compound represented by Chemical Formula 2; and a cyclohexane 1,4-diester-based compound represented by Chemical Formula 3, wherein the cyclohexane 1,4-diester-based compound represented by Chemical Formula 1, the cyclohexane 1,4-diester-based compound represented by Chemical Formula 2, and the cyclohexane 1,4-diester-based compound represented by Chemical Formula 3 are included at 0.5 to 70 wt %, 0.5 to 50 wt %, and 0.5 to 85 wt %, respectively, with respect to a total weight of the plasticizer composition, and wherein a weight average carbon number of $R_1$ and $R_2$ is in a range of 5.7 to 7.9:

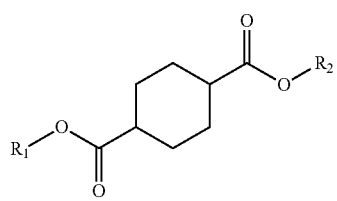

[Chemical Formula 1]

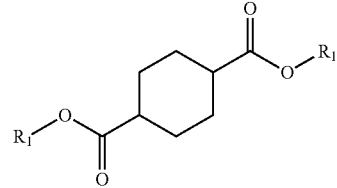

[Chemical Formula 2]

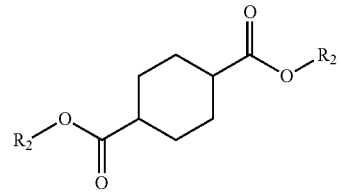

[Chemical Formula 3]

wherein $R_1$ is independently a butyl group or an isobutyl group, and $R_2$ is a 2-ethylhexyl group.

2. The plasticizer composition of claim 1, wherein the cyclohexane 1,4-diester-based compound represented by Chemical Formula 1, the cyclohexane 1,4-diester-based compound represented by Chemical Formula 2, and the cyclohexane 1,4-diester-based compound represented by Chemical Formula 3 are included at 10 to 50 wt %, 0.5 to 50 wt %, and 35 to 80 wt %, respectively, with respect to a total weight of the plasticizer composition.

3. The plasticizer composition of claim 1, wherein a weight ratio between a sum of the cyclohexane 1,4-diester-based compound represented by Chemical Formula 2 and the cyclohexane 1,4-diester-based compound represented by Chemical Formula 3, and the cyclohexane 1,4-diester-based compound represented by Chemical Formula 1 is 95:5 to 30:70.

4. A resin composition comprising:
   100 parts by weight of a resin; and
   5 to 150 parts by weight of the plasticizer composition of claim 1.

5. The resin composition of claim 4, wherein the resin includes one or more selected from the group consisting of ethylene vinyl acetate, polyethylene, polyketone, polypropylene, polyvinyl chloride, polystyrene, polyurethane, and a thermoplastic elastomer.

6. A material for producing an article comprising the resin composition of claim 4, wherein the article is one or more selected from the group consisting of electric wires, flooring materials, interior materials for automobiles, films, sheets, wallpaper sheets, and tubes.

* * * * *